(12) United States Patent
Alleyne et al.

(10) Patent No.: US 8,356,518 B2
(45) Date of Patent: Jan. 22, 2013

(54) METHOD AND APPARATUS FOR ULTRASONICALLY INSPECTING PIPES

(75) Inventors: David Alleyne, London (GB); Steve Banks, Guernsey (GB); Brian Pavlakovic, London (GB)

(73) Assignees: Genesis Oil & Gas Consultants Ltd (GB); Guided Ultrasonics Ltd (GB)

( * ) Notice: Subject to any disclaimer, the term of this patent is extended or adjusted under 35 U.S.C. 154(b) by 746 days.

(21) Appl. No.: 12/298,333

(22) PCT Filed: Apr. 24, 2007

(86) PCT No.: PCT/GB2007/001499
§ 371 (c)(1),
(2), (4) Date: Jan. 5, 2009

(87) PCT Pub. No.: WO2007/125308
PCT Pub. Date: Nov. 8, 2007

(65) Prior Publication Data
US 2009/0158850 A1    Jun. 25, 2009

(30) Foreign Application Priority Data
Apr. 28, 2006    (GB) .................................. 0608421.4

(51) Int. Cl.
*G01N 29/24*    (2006.01)
(52) U.S. Cl. .......................... 73/623; 73/865.8; 73/866.5
(58) Field of Classification Search .................... 73/623, 73/866.5, 40.5 R, 40.5 A, 865.8, 628, 622; 324/220, 221
See application file for complete search history.

(56) References Cited

U.S. PATENT DOCUMENTS 3,786,684 A * 1/1974 Wiers et al. .................. 73/866.5
3,810,384 A * 5/1974 Evans ............................. 73/611
(Continued)

FOREIGN PATENT DOCUMENTS
EP    1 333 277    8/2003
GB    2 020 023 A    6/1979
(Continued)

OTHER PUBLICATIONS

D.N. Alleyne et al., "Rapid Long Range Inspection of Chemical Plant Pipework Using Guided Waves", ROMA 2000 15th World Conference on NDT, Oct. 2000, Rome, Italy, 9 pages.

(Continued)

*Primary Examiner* — Helen C. Kwok
(74) *Attorney, Agent, or Firm* — Ostrolenk Faber LLP (57) ABSTRACT

An apparatus for inspecting a pipe comprising a body adapted for passage through the bore of a pipe to be inspected, a main transducer array comprising a plurality of circumferentially spaced transducers for transmitting ultrasound energy, the transducers being mounted on the body for movement between a retracted position, wherein the body can freely move through the bore of the pipe, and an extended position wherein the plurality of transducers are pressed into operative contact with the inner wall of the pipe. An actuator selectively urges the plurality of transducers to their extended positions. A control transmits ultrasound energy into the pipe to propagate a guided wave within the pipe walls in at least one longitudinal direction along the pipe when the transducers are in their operative position and receives the propagated wave and analyzes the wave to determine the presence or absence of defects in the pipe wall.

17 Claims, 4 Drawing Sheets

U.S. PATENT DOCUMENTS

| | | | | |
|---|---|---|---|---|
| 3,949,292 | A * | 4/1976 | Beaver et al. | 324/220 |
| 4,092,868 | A | 6/1978 | Thompson et al. | |
| 4,153,875 | A * | 5/1979 | Pigeon et al. | 324/220 |
| 4,306,459 | A | 12/1981 | Johnson et al. | |
| 4,807,484 | A * | 2/1989 | Goedecke | 73/865.8 |
| 4,953,412 | A | 9/1990 | Rosenberg et al. | 73/865.8 |
| 5,115,196 | A * | 5/1992 | Low et al. | 324/220 |
| 5,460,046 | A * | 10/1995 | Maltby et al. | 73/623 |
| 5,594,176 | A | 1/1997 | Kiefer | |
| 5,675,084 | A * | 10/1997 | Goedecke | 73/623 |
| 6,076,407 | A | 6/2000 | Levesque et al. | |
| 6,148,672 | A * | 11/2000 | Cawley et al. | 73/622 |
| 6,848,313 | B2 * | 2/2005 | Krieg et al. | 73/628 |
| 7,240,574 | B2 * | 7/2007 | Sapelnikov et al. | 73/865.8 |
| 7,317,308 | B2 * | 1/2008 | Fagbayi et al. | 324/71.1 |
| 7,458,289 | B2 * | 12/2008 | Houldey et al. | 73/865.8 |
| 2003/0101821 | A1 | 6/2003 | Thomas et al. | |

FOREIGN PATENT DOCUMENTS

| | | |
|---|---|---|
| GB | 2 255 825 A | 5/1992 |
| JP | 6190052 | 7/1994 |
| WO | WO 96/12951 | 5/1996 |
| WO | WO 99/31499 | 6/1999 |
| WO | WO 03/021249 A2 | 3/2003 |

OTHER PUBLICATIONS

British Search Report dated Aug. 14, 2006 for GB 0608421.4, 3 pages.
Notification Concerning Transmittal of International Preliminary Report on Patentability and International Preliminary Report on Patentability for International Application No. PCT/GB2007/001499, International Filing Date Apr. 24, 2007, report dated Oct. 28, 2008, 12 pages total.
International Search Report dated Nov. 7, 2007, issued in corresponding international application No. PCT/GB2007/001499.

* cited by examiner

METHOD AND APPARATUS FOR ULTRASONICALLY INSPECTING PIPES

CROSS REFERENCE TO RELATED APPLICATION

The present application is a 35 U.S.C. §§371 national phase conversion of PCT/GB2007/001499, filed 24 Apr. 2007, which claims priority of Great Britain Application No. 0608421.4, filed 28 Apr. 2006, incorporated by reference herein. The PCT International Application was published in the English language.

BACKGROUND OF THE INVENTION

The present invention relates to a method and apparatus for inspecting pipes, in particular deep water steel catenary risers (SCR) and gas pipelines (both offshore and onshore, including buried pipelines).

Due to environmental loading, subsea currents and increasing water depths, SCRs are susceptible to fatigue cracking at the touch down areas and at the stress joint locations where they connect to the host platform. The orientation and nature of the fatigue cracks that develop in the circumferential welds and associated heat affected zones are difficult to detect with current in-line or pigging inspection techniques. Frequently an insulating coating is applied to the SCRs and other flowlines to prevent hydrate formation within the pipe. Such coating restricts the use of externally applied inspection techniques.

Critical defects to be detected in SCRs are fatigue cracks in circumferential welds (or in associated heat affected zones) adjacent touchdown areas where the bending stresses are generally greatest and the fatigue life of the SCR is therefore shortest. These critical cracks generally form parallel to the weld and their orientation is therefore circumferential with reference to the pipe.

Corrosion in SCRs and other pipelines is also a major problem in the oil, gas, chemical and other industries. Many pipes are insulated which means that even external corrosion cannot be seen without removing the insulation, which is prohibitively expensive and may lead to damage to the pipe. Internal corrosion and erosion are also particular problems in SCRs and gas pipelines where aggressive fluids are conveyed by the pipelines.

The in-line inspection of gas transmission pipelines is the most appropriate way to check the integrity of the pipeline. The exposure and external inspection of buried pipe on land, is not only extremely costly but in many locations totally impracticable. In offshore locations there may not be the same constraints as those experienced on land to expose the pipeline but in both incidents great care is taken to ensure that the gas transmitted has reached a certain dew point and is dry. It is therefore beneficial that the in-line inspection method does not introduce any moisture into the pipeline during the inspection.

Many of the SCR infield flow lines and risers are between approximately 200 & 305 mm diameter, with manifold pipe work between approximately 100 and 160 mm in diameter. Manifold pipe work, especially on the production side, like the SCRs, normally has an insulating coating in place that can be up to 50.4 mm thick, therefore, like SCRs, external inspection methods can only be used in a limited capacity, for example at designated inspection ports. The smaller diameter lines at the manifold location also make it extremely difficult for the current in-line inspection pigs to pass through tight bends.

Platform caissons can be used for a number of applications offshore, to pump seawater for the platform firewater deluge system, or for discharge purposes. Although their integrity is not as critical as a gas or production riser, their can be serious consequences from their failure. Failures may cause caissons to break off and strike pipelines on the seafloor or lead to failure of the internal pumps that deliver seawater to topside fire fighting systems. The inspection of these components for cracking or wall loss is difficult due to the normally heavy external marine growth cover.

In order to mitigate the risk of failure or leakages it is desirable to inspect and detect fatigue cracking in SCRs and other pipes and flowlines and also to detect any reduction in the wall thickness of such pipes due to corrosion and/or erosion. It is particularly desirable to detect any cracks having a section greater than 1% of the pipe cross section.

Non destructive testing (NDT) techniques for steel pipes, and for inspecting welds in particular, have been developed and such techniques have found application in the inspection of pipelines. Examples of such techniques are X-ray testing, ultrasonic testing, magnetic particle testing, magnetic flux leakage and eddy current testing. However, such known techniques all possess disadvantages that render them unsuitable for use in the inspection of SCRs due to the harsh environment in which SCRs operate and the lack of accessibility to the areas to be inspected.

Magnetic flux leakage (MFL) devices are very common in the oil and gas field, usually provided on pigs for passage through the pipe to be inspected. However, they are not able to reliably detect circumferential cracks and are most suited for detection of corrosion metal loss. Furthermore, MFL devices lack the flexibility to accommodate different pipe diameters. Finally, MFL devices only work on magnetic materials and hence cannot be used for pipes made from a non magnetic stainless steel grade.

Ultrasonic waves can propagate through the wall of a pipe. The presence of defects, such as cracks, in the path of the waves can be detected, either by a detector remote from a source of ultrasonic waves or by detecting reflections from the defect by a detector at or adjacent the source. WO 99/31499 discloses a pig using high frequency (0.5 MHZ to 1 MHz) ultrasonic waves to inspect short lengths of pipe facing the inspection head (typically less than 0.5 m). Such high frequency waves provide high resolution and detection sensitivity but suffer high attenuation and therefore short range. In order to inspect the whole length of a pipe, the pig has to be moved along the pipe while continuously transmitting and detecting ultrasonic waves. Such a system is bulky and expensive and would be unsuitable for many applications, such as gas pipelines, because the pipe needs to be filled with a liquid, such as oil or water, to ensure ultrasonic coupling between the piezoelectric transducers and the pipe wall. Furthermore, such system is very sensitive to contamination on the pipe walls because dirt or trapped air bubbles can cause false defect readings.

Ultrasonic guided waves in the pipe wall, such as Lamb waves, are particularly useful for inspecting pipes for defects because they can be excited at one location on the pipe and will propagate many meters along the pipe, returning echoes indicating the presence of corrosion, fatigue cracks or other pipe defects. Ultrasonic guided waves are guided vibrational modes of a body of material wherein ultrasonic energy is trapped between the boundaries of said body of material and guided through said body of material by the large mismatch in mechanical impedance between the wall of the body of material and a surrounding medium. The terminology is more fully explained in the article by M. G. Silk and K. F. Bainton in the journal "Ultrasonics" of January 1979 at pp 11-19 entitled "The propagation in metal tubing of ultrasonic wave modes equivalent to Lamb waves".

WO 96/12951 (incorporated herein by reference) discloses the use of long range ultrasonic guided waves to detect faults and reduction in the wall thickness in a pipe. The method relies on the property of low frequency (<100 kHz) guided waves to propagate inside the pipe wall parallel to the pipe axis, with small attenuation, thus making it possible to detect defects located up to tens of meters from the inspection head, said fault detection being made by the detection of the echo reflected by the defect. The method is implemented by dry clamping a ring of piezoelectric transducers to the outer surface of the pipe. However, this technique requires access to the outer surface of the pipe at regular intervals along the length of the pipe. This may not be practical for insulated pipelines, particularly for SCRs which may operate at great depth, making removal of the insulation and subsea depositions on the pipe surface impractical. Such method is also unsuitable for buried pipelines for the same reason.

It is therefore desirable to provide a tool using ultrasonic guided waves that can inspect the pipeline from the inside.

BRIEF SUMMARY OF THE INVENTION

According to a first aspect of the present invention there is provided an apparatus for inspecting a pipe comprising a body adapted for passage through the bore of a pipe to be inspected, a main transducer array comprising a plurality of circumferentially spaced transducers for transmitting ultrasound energy, the transducers being mounted on the body for movement between a retracted position, wherein the body can freely move through the bore of the pipe, and an extended position wherein the plurality of transducers are pressed into operative contact with the inner wall of the pipe, actuating means being provided for selectively urging the plurality of transducers to their extended positions, control means being provided for controlling the transducers to transmit ultrasound energy into said pipe to propagate a guided wave within the pipe walls in at least one longitudinal direction along the pipe when the transducers are in their operative position and for receiving the propagated wave and analysing said wave to determine the presence or absence or defects in the pipe wall.

Preferably said actuating means comprises one or more hydraulically actuated pistons for urging said plurality of transducers against the inner wall of the pipe. Preferably each of said hydraulically actuated pistons is mounted in a respective cylinder communicating with a common manifold, said manifold being pressurisable to urge the pistons and hence the transducers against the pipe wall with substantially equal pressure.

Preferably said plurality of transducers are biased towards their retracted position, preferably by one or more spring means.

Preferably each transducer is provided with a contact head for contact with the inner wall of the pipe to be inspected, the outer surface of said contact head defining the intersection of a rectangular parallelepiped and the outer edge of a toroid, wherein the major and minor radii of the toroid are at least 10% smaller than the smallest radius of the pipe to be inspected in order to obtain an approximate point contact of the contact head with the inner wall of the pipe. Preferably said contact head is formed from an electrically insulating material, such as alumina.

Preferably the transducers comprise shear polarised piezoelectric transducers capable of both emitting ultrasonic energy and detecting reflected ultrasonic waves.

In a preferred embodiment said plurality of transducers of the main transducer array are arranged in two rows around the circumference of the body. The transducers are preferably oriented to generate guided waves in the torsional mode T(0, 1) such that unidirectional excitation can be achieved with two rows of transducers. In order to ensure that the transducers are pressed against the inner surface of the pipe with equal force, groups of three adjacent transducers, two from one row and one from the other, are mounted on a common carrier member, the carrier member being attached to a base member via a ball and socket mounting means to permit tilting movement of the carrier member in any direction relative to an axis equally spaced from each of said three adjacent transducers.

In addition to said main transducer array, a further transducer array may be provided comprising additional transducers mounted within an expandable elastomeric toroid provided around a peripheral region of said body, said toroid preferably being filled with a liquid, such as oil, the pressure of said liquid being adjustable to selectively expand the toroid into operative engagement with the inner surface of the pipe to be inspected. Preferably said additional transducers comprise high frequency (approximately 1-10 MHz) ultrasonic transducers which can be used to measure the standard pipe wall thickness (via normal incident bulk waves) as well as the average pipe wall thickness and attenuation and velocity of the guided waves through the pipe wall (via circumferentially oriented guided waves). Such measurements can be used to calibrate the main transducer array.

According to a second aspect of the present invention there is provided a method of inspecting a pipe using an inspection apparatus according to the first aspect of the invention, said method comprising the steps of:— a) inserting said inspection apparatus into the bore of a pipe to be inspected;
b) moving said plurality of transducers to their second or extended positions to be in operative contact with the inner wall of the pipe;
c) operating said plurality of transducers to transmit ultrasound energy into said pipe to propagate a guided wave in the pipe in at least one longitudinal direction along the pipe;
d) detecting reflections of the propagated wave and analysing said reflections to determine the presence or absence or defects in the pipe wall;
e) moving the plurality of transducers to their retracted position and;
f) conveying the body through the pipe to a further inspection position and repeating steps (b) to (e).

Preferably said reflections of the propagated wave are detected by said plurality of transducers.

According to a third aspect of the present invention there is provided a transducer for transmitting ultrasound energy into a pipe for use with a pipe inspection apparatus, said transducer comprising a contact head for contacting an inner surface of said pipe, the outer surface of said contact head defining the intersection of a rectangular parallelepiped and the outer edge of a toroid, wherein the major and minor radii of the toroid are at least 10% smaller than the smallest radius of the pipe to be inspected in order to obtain an approximate point contact of the contact head with the inner wall of the pipe. Preferably said contact head is formed from an electrically insulating material, such as alumina.

BRIEF DESCRIPTION OF THE DRAWINGS

The present invention will now be described, by way of example, with reference to the accompanying drawings, in which.

DETAILED DESCRIPTION OF THE INVENTION

Figure 1:
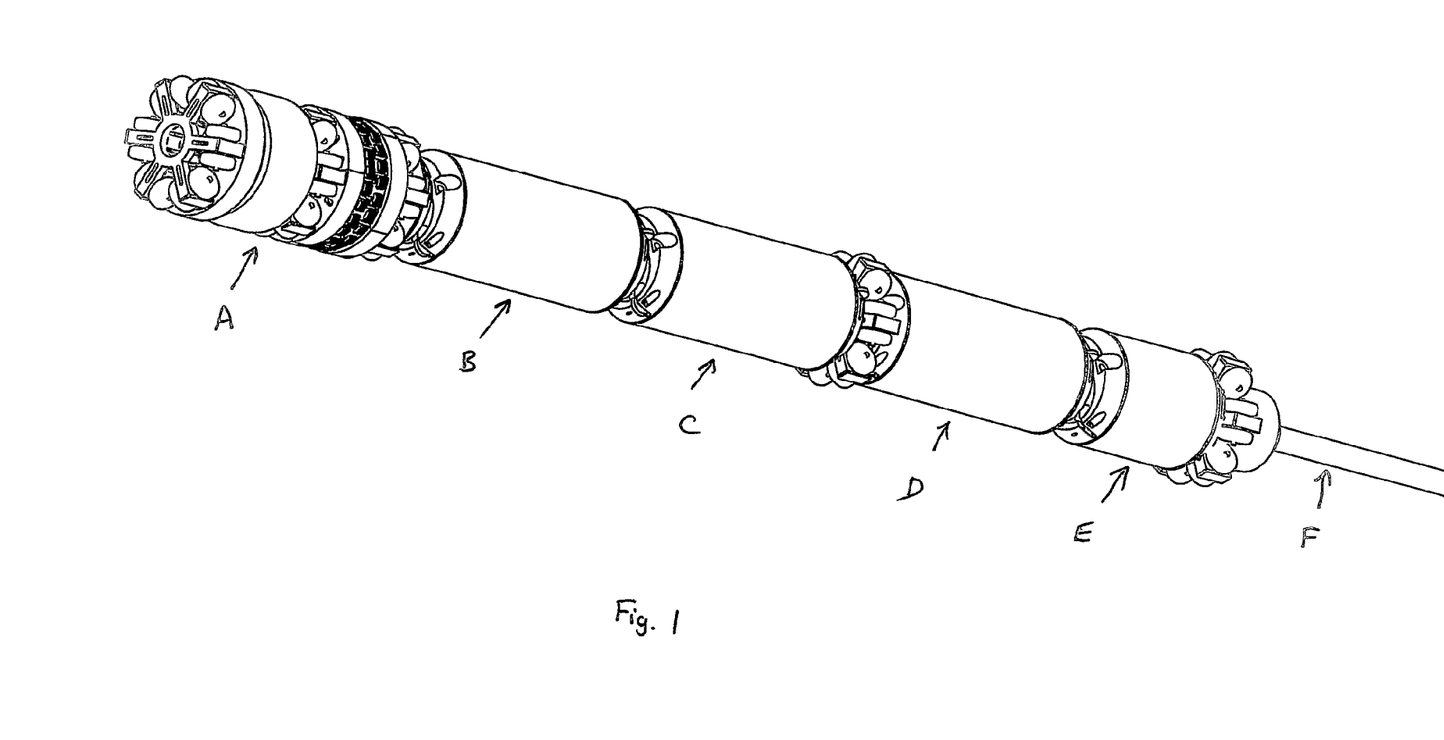
FIG. 1 is a perspective view of an inspection apparatus according to a first embodiment of the present invention.

A first embodiment of the present invention will be described with reference to the drawings. The apparatus comprises a pig adapted to be passed through the bore of a pipe to be inspected, such as a steel catenary riser. The pig comprises multiple units that are linked together. At the front of the pig is a transducer head A followed by a pressure vessel B providing a power source of the pig. Further sections C, D, E may to house system electronics and auxiliary equipment. At the end of the pig is an anchor F for a tether.

Figure 2:
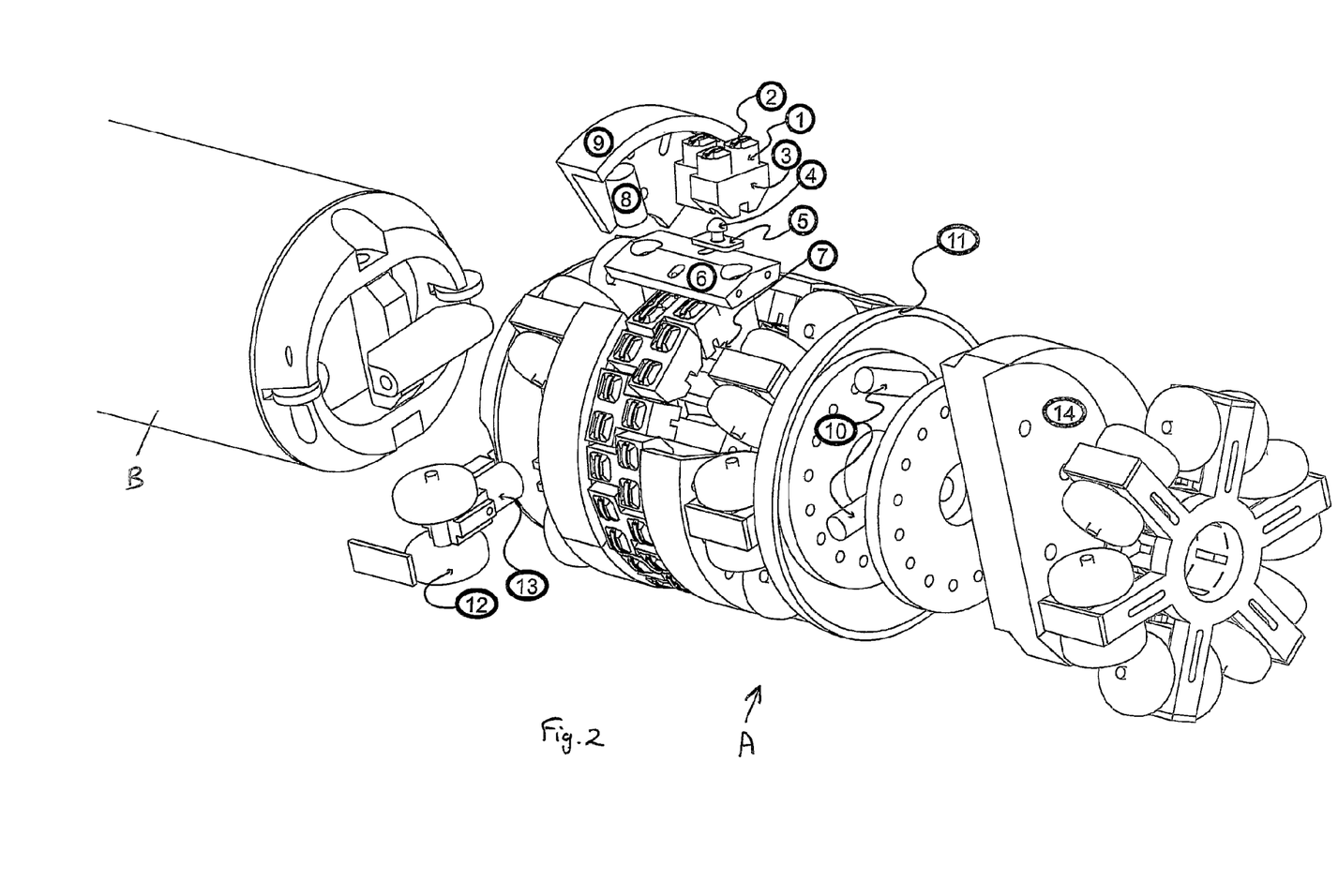
FIG. 2 is a detailed exploded view of the transducer head of the apparatus of FIG. 1.

The transducer head is shown in more detail in FIG. 2. The transducer head comprises a main transducer array comprising ultrasonic shear piezoelectric transducer elements 1 arranged in one or more rows (two in this case) circumferentially around the pipe.

The design of the transducer elements is similar to that disclosed in WO 96/12951. Each transducer element is arranged to provide a force on the pipe wall in a circumferential direction to achieve torsional mode excitation of the pipe wall. Use of the axis-symmetric torsional mode T(0,1) allows the use of only one ring or transducers for bidirectional excitation or two rings, as shown in the drawings, for unidirectional excitation.

It is also possible to excite axially symmetric longitudinal (Lamb type) waves in the pipe wall. To achieve this the transducers must be oriented to apply force to the pipe wall in a direction parallel to the longitudinal axis of the pipe. However, such configuration is more complex, requiring at least two rings of transducers for bidirectional excitation of the single mode L(0,2) with suppression of the L(0,1) mode and three rings for unidirectional excitation of the single mode L(0,2) with suppression of the L(0,1) mode.

It is also possible to excite various flexural mode waves in the pipe wall, by varying the phase and optionally the amplitude of the signals that are applied to each of the transducers around the circumference of the pipe.

In order to provide good contact with the inner wall of the pipe to enable each transducer element to exert a shear force on the pipe wall, each transducer element 1 is provided with a double curved alumina faceplate 2 that isolates the transducer element electronically from the pipe, while providing an approximate point contact with the inside wall of the pipe.

Figure 3:
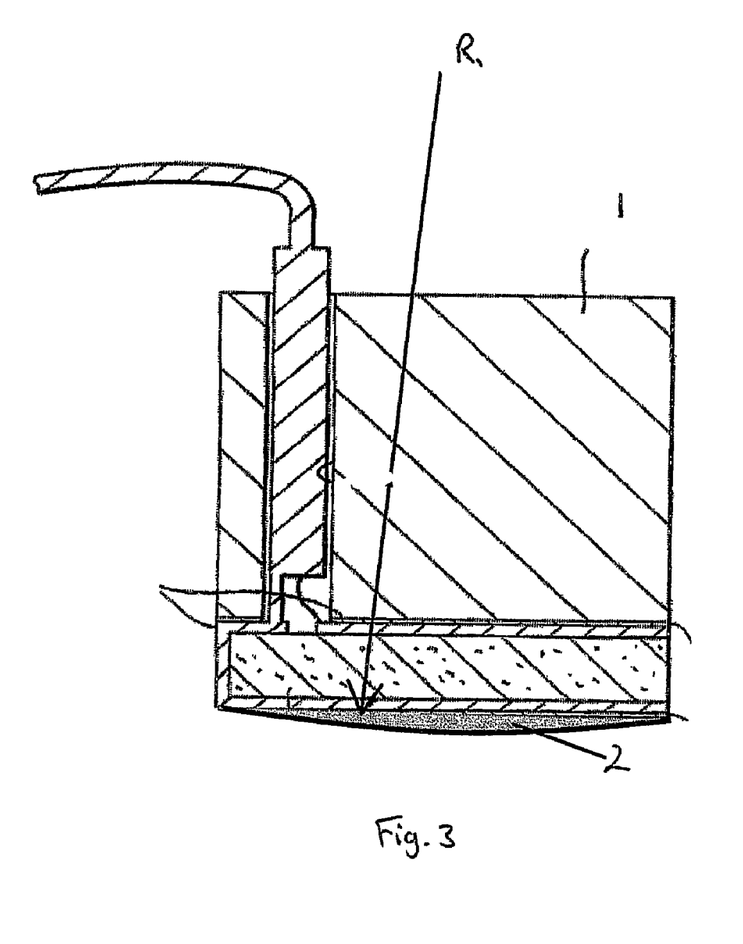
FIG. 3 is a side sectional view of a piezoelectric transducer of the main transducer array apparatus of FIG. 1.
Figure 4:
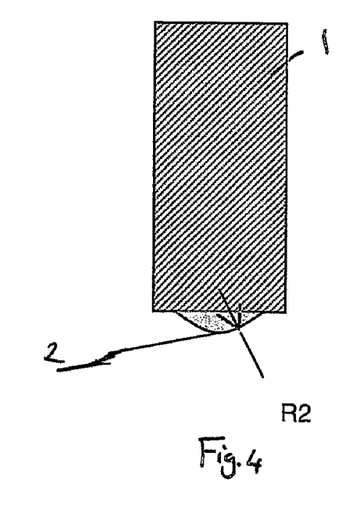
FIG. 4 is an end sectional view of the piezoelectric transducer of FIG. 3.

As shown in FIGS. 3 and 4, the shape of this faceplate 2 is the intersection of a rectangular parallelepiped and the edge of the toroid. The major $R_1$ and minor $R_2$ radii of the toroid are chosen to ensure that their sum is at least 10 percent smaller than the smallest radius of the pipe that will be inspected. This ensures that there is a close approximation to a point contact.

The transducer elements 1 are attached to transducer tripods 3 in groups of three, two from one row and one from an adjacent row. Each transducer tripod 3 is mounted on a radially extending domed pin 4 having a longitudinal axis substantially equidistance from each of the three elements in the group. The pin 4 is held in place by a cover 5 to allow the tripod 3 to tilt slightly in any direction. This flexibility helps ensure that all three transducer elements 1 touch the pipe wall and have approximately equal force applied through them. Orientations pins on the tripod (not shown) prevent it from spinning.

Pairs of tripods 3 are mounted (via the domed pins) onto a respective transducer piston 6. An oval shaft of each piston 6 is sealed by o-ring seals and fits into an associated cylinder in a transducer manifold 7, which is partially hidden in FIG. 1. When hydraulic pressure is applied to the centre of the transducer manifold 7, the transducer pistons 6 and associated transducer elements 1 are extended and brought into contact with the pipe wall with equal predetermined contact force (preferably 40 N). A pair of retraction springs 8 react against a retaining band 9 to retract the transducer pistons back into the manifold when hydraulic pressure is released.

The hydraulic pressure may either be provided from the surface via an umbilical or via a small on board hydraulic pump or screw. Suitable pressure limiters may be used to control the amount of force that is applied to the transducer elements.

Figure 5:
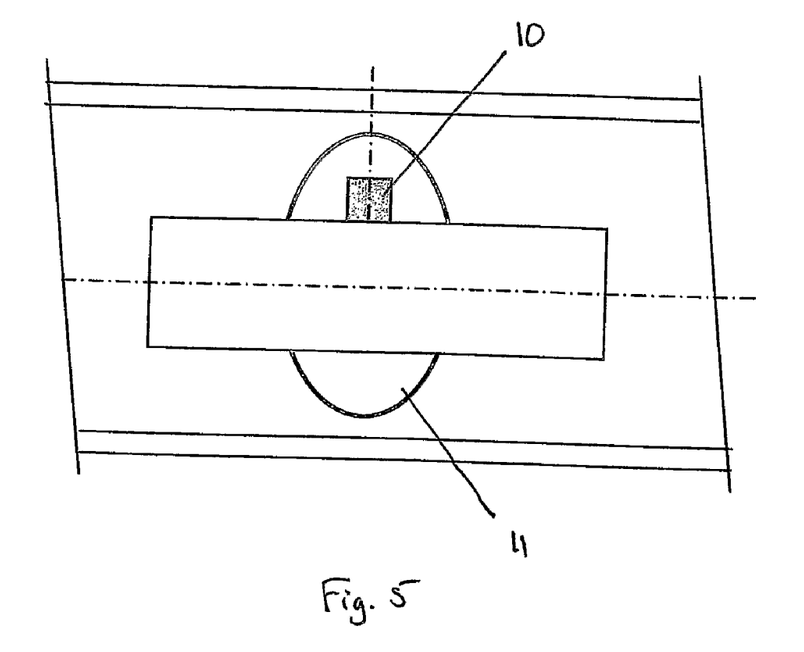
FIG. 5 is a schematic view of the secondary transducer array of the apparatus of FIG. 1.
Figure 6:
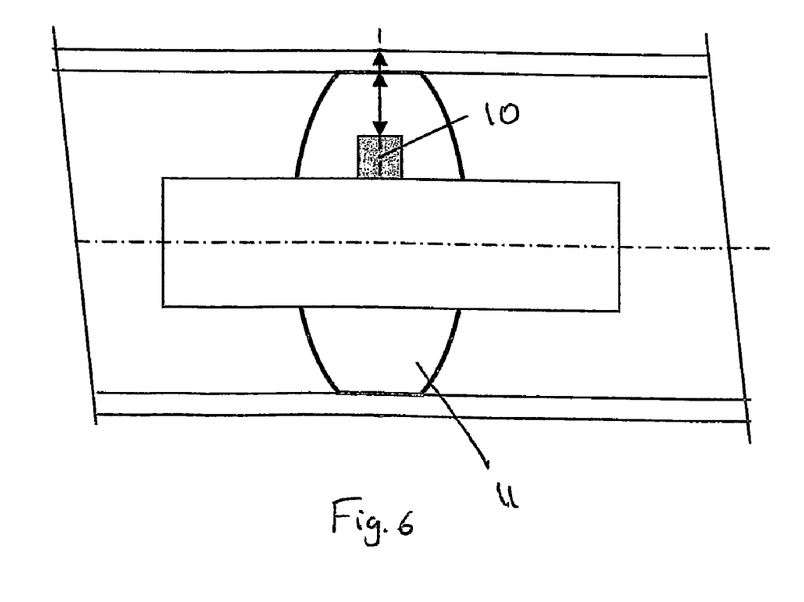
FIG. 6 is a schematic view of the secondary transducer array of FIG. 5 showing the inflatable toroid in its operative expanded state.

In addition to the main transducer array, a secondary transducer array comprising a plurality of high frequency calibration transducers 10 is also provided on the transducer head. These transducers 10 are housed in a fluid filled cavity surrounded by a toroidal rubber membrane 11, which has been cut away in FIG. 1. When the pig is stopped to perform a test, the cavity is expanded by hydraulic pressure so that the rubber membrane makes good contact with the pipe wall. The calibration measurements are made through the rubber (preventing liquid contamination of the pipeline). A rubber with low ultrasonic attenuation is used for the membrane in order to get good results. Both normal incident and/or angular incident ultrasonic waves may be generated. Normal incident waves can directly measure wall thickness. Angular incident waves may be used to create circumferentially or axially propagating guided waves to determine the average wall thickness around the circumference of the pipe. The transducers may be rotated within their cavity (or an ultrasonic mirror may be rotated) if multiple circumferential locations are to be inspected.

Many elements are present to assist the movement and orientation of the pig. These include the centering wheels 12 that are spring loaded 13 onto the pipe walls to keep the pig aligned. One or more of these wheels may contain encoders that may be used to help quantify the position along the pipe (encoder connections not shown in drawing). In addition, one or more of these wheels may powered to assist the movement of the pig (especially when configured as a crawler).

A plastic plough 14 is one example of a cleaning attachment that could be added to the front of the pig.

The control electronics used within the inspection apparatus are a specialized version of the Wavemaker G3 electronics manufactured by Guided Ultrasonics Limited. However, the layout has been revised in order to fit in the tightly constrained dimensions required to allow the apparatus to fit through the pipeline. Communication to the surface (when tethered) is made via a serial connection.

The present invention primarily uses guided wave propagation along the axis of the pipe from an array of transducers for the inspection of pipelines from the inside.

The apparatus and method of the present invention is able to detect a wide variety of defects, especially cracks, that are difficult for known through thickness measurements. Since the main propagation direction is along the axis of the pipe, circumferential defects, such as cracks in welds, are much easier to detect and size as opposed to through thickness or circumferentially oriented waves that only reflect from the leading and trailing edge of the crack.

The defect detection method and apparatus of the present invention is less sensitive to cleanliness/material property changes than electromagnetic (for example MFL/EMAT) based systems. The transducers are pressed against the surface with enough force to push debris out of the way. This large force allows a shearing motion to be directly transmitted into the pipe wall. The system does not need to rely on the consistency of magnetic or electrical properties of the pipe.

Both through transmission (relying on detection of changes to guided wave as it travels) and reflection data can be used in the present invention.

Through transmission is used for
1. Calibration of transducers;
2. Coating condition determination to look for degraded or dis-bonded coating that could lead to future failures;
3. Attenuation due to presence of defects such as microcracking;

However, through transmission is not used as the primary defect detection method. Reflections back to the transmitting transducer (and those around it) are used for the main defect determination. This method is much less sensitive to false readings that transmission methods.

Frequency limits are mainly set by the pipe wall thickness to ensure that the ultrasonic frequency of the main transducer array is below the cut-off frequency of the T(0,2) guided wave mode.

The number of transducers around the circumference of the main transducer array is set to ensure that there are at least 2 transducers per wavelength of the fastest wave of interest (at the highest frequency of interest).

A few high frequency ultrasonic measurements from the secondary transducer array will be synthesized with the guided wave results from the main transducer array to provide more quantitative results since the main guided wave data responds to changes in the condition of the pipe from the current test location.

The secondary transducer array provides data that is used to calibrate the main transducer array, such as the pipe thickness and the velocity and the attenuation of the guided waves.

The secondary transducer array can be used to make ultrasonic thickness measurements, via normal incident longitudinal waves, at one or more points around the circumference of the pipe. These thickness measurements are useful not only to calibrate the main transducer array, but also to assist in detection of defects that may be difficult to detect with the main transducer array, such as for example erosion type grooves running consistently along the length of the pipe.

The secondary transducer array can also be used to send, receive and measure guided waves that propagate circumferentially around the pipe. This way, it is possible to make numerous tests covering multiple modes over a wide frequency range. These tests can be used in different ways and for different purposes, such as:— a) the analysis of group velocity of certain circumferential flexural guided wave modes can be used to obtain the average wall thickness of the pipe;
b) circumferential guided waves can also be used to determine if there is much variation in wall thickness around the circumference of the pipe. This will aid the detection of the certain types of defects, such as erosion, that can be relatively consistent along the length of the pipe;
c) Finally, these measures can be used for an accurate calibration of the main transducer array. Indeed, the multiple circumferentially oriented guided wave modes sent and received by the secondary transducer array have frequency dependent velocities that vary with the properties of the pipe and of the coating outside the pipe. Therefore, by iteratively matching the measures to a theoretical model of what guided modes can propagate, the material properties of the pipe and of the coating, as well as their bonding conditions, can be extracted. Once these properties are known, they can be fed back into the theoretical model to predict how they will affect the main guided waves being used by the main transducer array.

The processing algorithm is a simple extension of the guided wave processing that is used for inspection from the outside of the pipe. This is based on a phased (or time delayed) combination from multiple output and input transducers. Proper combination of the time traces allows different order guided wave modes to be extracted, which allows characterization of any reflectors that are encountered.

It is also possible to treat the main transducer array as elements in a phased array in order to steer the energy to specific locations near to the transducer head. This allows better discrimination of any defects that are found by the initial screening of the pipe.

Deployment Methods

The present invention lends itself to a number of deployment methods which are described below. One of the main advantages of the present invention over other technologies is that it can be re-packaged easily for deployment onto different applications to meet specific operational constraints of the client.

Free Swimming Pig

In the first embodiment, as discussed above, the inspection apparatus can be provided in a free swimming pig system. The tool can be broken down into separate components/segments joined by a semi-rigid connection that allows communication between each segment. The pig can be propelled by either gas (for gas injection) or recovered product.

In use, the pig will stop at certain points based on time/distance calculations or by attached odometers by allowing some of the pressure to bypass the tool and divert into an actuator that pushes the transducers out; the transducers will be deployed from the transducer head and a test carried out. Once the test is complete the pressure behind the transducers will be released and the transducers will be free to be pushed back into the transducer head as the tool is moved forward be allowing the pressure to build up again.

Tethered

In a further embodiment, the inspection apparatus can be deployed with a tether and winch system following a similar design concept to that of the free swimming pig. This system can be initially targeted at fatigue crack detection at the touch-down areas of the SCRs. The apparatus can be deployed into a riser attached to a tether and winch. The tether will provide power and communication to the apparatus as well as provide a method to recover the apparatus. The inspection apparatus will be sent a specific distance into the riser/pipeline, past the touch down location, and then recovered in set stages, typically at 10 m intervals. At each 10 m interval the apparatus will be stationary and the transducers will be deployed from the transducer head by a hydraulic pressure through the tether or via a small on-board hydraulic pump, and a test carried out. Once the test is complete the transducers will be retracted, by the release of hydraulic pressure and the tool will be recovered a further 10 m until the riser touch down area (or the whole riser system) is complete. Inspection of critical welds will normally be conducted from both sides and the data merged together.

Diver Deployment

A diver deployed embodiment of the present invention can be specific to smaller diameter manifold pipe work where access is through a flange connection, one the system has been isolated. A typical example may be when some part of the production system within the manifold header has failed due to internal corrosion by an aggressive product and it is necessary to inspect the remainder of the pipe work for similar failure modes. A thorough inspection can normally only be carried out internally due to external insulating coating. This insulating coating would require power tools to remove and there would be a chance of damaging the pipe underneath if these operation where carried out.

The transducer head is attached to a suitable handle and then inserted into the pipe. The communication cable from the transducer head will run back to a diver deployed control unit in the work basket a few meters away. The transducer head can then be pumped up to the required pressure (hydraulics) to urge the transducers into conduct with the pipe wall.

Remotely Operated Vehicle (ROV)

Like the diver method the transducer head can be used separately and deployed from a ROV for the inspection of caissons (those without protective grill). There are several advantages from applying the technology from within the caisson rather that externally and centre around the preparing the contact point of marine growth before applying the transducer head. There may also be some advantages when manufacturing and deploying the transducer head for the inspection of caissons if the inspection is carried out internally.

Crawler

In a further embodiment, the inspection apparatus may be deployed by crawlers within the pipe/risers if the operational conditions required.

ADVANTAGES

The inspection apparatus according to the present invention relies on the pressure of the transducers to couple to the pipe wall rather than the requirement of a separate coupling. This allows the technique to be deployed internally on gas transmission lines that need to remain dry, and lines that have not been cleaned to any standard.

The overall design of the transducer head and attachments are much simpler and more easily packaged than competing techniques. This allows deployment in smaller diameter lines and for the tool to navigate different geometries more easily than current in-line inspection technologies.

As each test is carried our, guided waves are sent sequentially in both directions of the transducer head giving overlapping data throughout the whole inspection process.

As the guided waves propagate along the line there is no need for pin point accuracy for the tool to be at a specific weld location to detect any fatigue cracking that could be within the weld or associated heat affected zone.

During tethered operations anomalies can be detected and engineers informed while the pig is still on location allowing follow up actions by the in-line tool if required.

The presentation of the data is easily understood by engineers with only a basic understanding of the guided ultrasonic concept.

By deploying internally at the caisson opening a hydraulic spinning cleaning tool is more efficient at cleaning marine growth and the transducer head will have a better coupling to the caisson wall.

The invention claimed is:

1. An apparatus for inspecting a pipe comprising
a body configured and operable for passage through a bore of a pipe to be inspected,
a main transducer array comprising a plurality of circumferentially spaced transducers for transmitting ultrasound energy, the transducers being mounted on the body for movement of the transducers between a retracted position, wherein the body can freely move through the bore of the pipe, and an extended position wherein the plurality of transducers are pressed into operative contact with an inner wall of the pipe,
an actuator for selectively urging the plurality of transducers to the extended position,
a controller for transmitting ultrasound energy into said pipe to propagate a guided wave within pipe walls of the pipe in at least one longitudinal direction along the pipe when the transducers are in the extended positions and for receiving the propagated wave and analyzing said wave to determine the presence or absence of defects in the pipe wall,
wherein said transducers comprise shear polarized piezoelectric transducers capable of both emitting ultrasonic energy and detecting reflected ultrasonic waves,
wherein each transducer has a contact head for contact with the inner wall of the pipe to be inspected, an outer surface of said contact head defining an intersection of a rectangular parallelepiped and an outer edge of a toroid, wherein the major and minor radii of the toroid are at least 10% smaller than the smallest radius of the pipe to be inspected in order to obtain an approximate point contact of the contact head with the inner wall of the pipe.

2. An apparatus as claimed in claim 1, wherein said actuator comprises one or more hydraulically actuated pistons for urging said plurality of transducers to the extended positions against the inner wall of the pipe.

3. An apparatus as claimed in claim 2, wherein each of said hydraulically actuated pistons is slidably mounted in a respective cylinder communicating with a common manifold, said manifold being pressurisable to urge the pistons and hence said transducers against the pipe wall with substantially equal pressure.

4. An apparatus as claimed in claim 1, wherein said plurality of transducers are biased towards the retracted positions.

5. An apparatus as claimed in claim 1, wherein said contact head is formed from an electrically insulating material.

6. An apparatus as claimed in claim 1, wherein said plurality of transducers of the main transducer array are arranged in two rows around a circumference of the body.

7. An apparatus as claimed in claim 6, wherein the transducers are oriented to generate guided waves in a torsional mode $T(0,1)$.

8. An apparatus as claimed in claim 6, wherein groups of three adjacent said transducers, two transducers from one row and one transducer from the other row, are mounted on a common carrier member, the carrier member being attached to a base member via a ball and socket mount to permit tilting movement of the carrier member in any direction about an axis equally spaced from each of said three adjacent transducers.

9. An apparatus as claimed in claim 1, comprising a further transducer array comprising additional transducers mounted within an expandable elastomeric toroid being filled with a liquid, and a pressure of said liquid being adjustable to selectively expand the toroid into operative engagement with an inner surface of the pipe to be inspected.

10. An apparatus as claimed in claim 9, wherein said additional transducers comprise high frequency of approximately 1-10 MHz ultrasonic transducers which are operable to measure a standard pipe wall thickness via normal incident bulk waves and an average pipe wall thickness and average wave velocity and attenuation through the pipe wall via circumferentially oriented guided waves to calibrate the main transducer array.

11. A method of inspecting a pipe using an inspection apparatus according to claim 1, said method comprising the steps of:
 a) inserting said inspection apparatus into the bore of a pipe to be inspected;
 b) moving said plurality of transducers to the extended positions to be in operative contact with the inner wall of the pipe;
 c) operating said plurality of transducers to transmit ultrasound energy into said pipe to propagate a guided wave in the pipe in at least one longitudinal direction along the pipe;
 d) detecting reflections of the propagated wave and analyzing said reflections to determine the presence or absence of defects in the pipe wall;
 e) moving the plurality of transducers to their retracted positions and;
 conveying the body through the pipe to a further inspection position and repeating steps (b) to (e).

12. A method as claimed in claim 11, wherein said reflections of the propagated wave are detected by said plurality of transducers.

13. A transducer for transmitting ultrasound energy into a pipe for use with a pipe inspection apparatus, said transducer comprising a contact head for contacting an inner surface of said pipe, an outer surface of said contact head defining an intersection of a rectangular parallelepiped and an outer edge of a toroid, wherein major and minor radii of the toroid are at least 10% smaller than the smallest radius of the pipe to be inspected in order to obtain an approximate point contact of the contact head with an inner wall of the pipe.

14. A transducer as claimed in claim 13, wherein said contact head is formed from an electrically insulating material.

15. An apparatus as claimed in claim 1, wherein said contact head is formed of alumina.

16. An apparatus as claimed in claim 1, wherein said transducers comprise shear polarized piezoelectric transducers capable of both emitting ultrasonic energy and detecting reflected ultrasonic waves.

17. The apparatus of claim 1, wherein the guided waves have a frequency less than 100 kHz.

* * * * *

UNITED STATES PATENT AND TRADEMARK OFFICE
CERTIFICATE OF CORRECTION

PATENT NO. : 8,356,518 B2  Page 1 of 1
APPLICATION NO. : 12/298333
DATED : January 22, 2013
INVENTOR(S) : Alleyne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 813 days.

Signed and Sealed this
First Day of September, 2015

Michelle K. Lee
*Director of the United States Patent and Trademark Office*